United States Patent
Banerjee

(10) Patent No.: US 6,405,074 B1
(45) Date of Patent: Jun. 11, 2002

(54) DETECTION OF CANCER USING CELLULAR AUTOFLUORESCENCE

(76) Inventor: Bhaskar Banerjee, 420 N. Village Cir., Columbia, MO (US) 65203

( * ) Notice: Subject to any disclaimer, the term of this patent is extended or adjusted under 35 U.S.C. 154(b) by 0 days.

(21) Appl. No.: 09/097,931

(22) Filed: Jun. 16, 1998

Related U.S. Application Data

(60) Provisional application No. 60/058,021, filed on Aug. 29, 1997.

(51) Int. Cl.$^7$ ................................................ A61B 5/00
(52) U.S. Cl. ....................... 600/477; 436/64; 250/461.2
(58) Field of Search ................................ 600/473, 475, 600/476, 477, 310; 250/458.1, 461.2, 484.2; 436/64, 63

(56) References Cited

U.S. PATENT DOCUMENTS

| | | | |
|---|---|---|---|
| 4,786,813 A | * 11/1988 | Svanberg et al. | 250/461.1 |
| 4,930,516 A | 6/1990 | Alfano et al. | |
| 5,042,494 A | 8/1991 | Alfano | |
| 5,131,398 A | 7/1992 | Alfano et al. | |
| 5,215,095 A | * 6/1993 | Macvicar et al. | 600/473 |
| 5,438,989 A | * 8/1995 | Hochman et al. | 600/407 |
| 5,465,718 A | * 11/1995 | Hochman et al. | 600/407 |
| 5,504,337 A | * 4/1996 | Lakowicz et al. | 356/318 |
| 5,507,287 A | 4/1996 | Palcic et al. | |

(List continued on next page.)

OTHER PUBLICATIONS

The New England Journal of Medicine, Sounding Board, Colon Cancer, Dysplasia, and Surveillance in Patients with Ulcerative Colitis, Jun. 25, 1987, pp. 1654–1658.

Colonic Fluorescence Spectroscopy, Gastroenterology, Jul. 1990, Laser–Induced Fluorescence Spectroscopy of Human Colonic Mucosa, pp. 150–157.

IEEE Journal of Quantum Electronics, vol. QE–23, No. 10, Fluorescence Spectra from Cancerous and Normal Human Breast and Lung Tissues, pp. 1806–1811.

Lasers in Surgery and Medicine 13:647–655 (1993), Study of the Fluorescence Properties of Normal and Neoplastic Human Cervical Tissue, pp. 647–655.

Gastrointestinal Endoscopy, vol. 36, Nov. 2, 1990, Gastrointestinal Tissue Diagnosis by Laser–Induced Fluorescence Spectroscopy at Endoscopy, pp. 105–110.

(List continued on next page.)

*Primary Examiner*—Ruth S. Smith
(74) *Attorney, Agent, or Firm*—Harness, Dickey & Pierce, P.L.C.

(57) ABSTRACT

Apparatus and methods especially useful for detection of cancer using cellular autofluorescence are described. In one embodiment, the apparatus includes a source of white light which produces a beam of light transmitted to a tissue via one group of optic fibers in a two-way fiber optic bundle. The two-way fiber optic bundle may be passed through a conventional endoscope. The beam of light excites the tissue and results in an emission of cellular autofluorescence at a wavelength of about 330 nm. A light sample from the tissue is directed back through the two-way fiber optic bundle and then passes through a photodetector. The photodetector produces a signal, representative of the intensity of cellular autofluorescence, which can be passed to a monitor as a wave form or meter response. The apparatus may further comprise a charge-coupled device and video imaging technology to produce real time video images of tissue being examined.

14 Claims, 4 Drawing Sheets

U.S. PATENT DOCUMENTS

| | | | | |
|---|---|---|---|---|
| 5,612,540 A | * | 3/1997 | Richards-Kortum et al. | 250/461.2 |
| 5,647,368 A | * | 7/1997 | Zeng et al. | 600/476 |
| 5,699,795 A | * | 12/1997 | Richards-Kortum et al. | 600/478 |
| 5,784,162 A | * | 7/1998 | Cabib et al. | 356/346 |
| 5,999,844 A | * | 12/1999 | Gombrich et al. | 600/476 |

OTHER PUBLICATIONS

Gastrointestinal Endoscopy, vol. 41, Nov. 6, 1995, Spectroscopic Diagnosis of Esophageal Cancer: New Classification Model, Improved Measurement System, pp. 577–581.

Diabetes, Concurrent Session, Sep. 20, 1996, Autofluorescence Spectroscopy of Colon Cells and Polyps, B. Banerjee.

* cited by examiner

DETECTION OF CANCER USING CELLULAR AUTOFLUORESCENCE

CROSS REFERENCE TO RELATED APPLICATION

This application claims the benefit of U.S. Provisional Application No. 60/058,021, filed Aug. 29, 1997.

FIELD OF THE INVENTION

This invention relates generally to detection of cancerous cells and more particularly, too detecting cancerous cells using cellular autofluorescence.

BACKGROUND OF THE INVENTION

The survival rate for cancer patients increases with early detection of cancer. Known methods of gaining early detection of cancer are limited to techniques such as surveillance endoscopy and random tissue biopsies, both of which are costly and inefficient. In addition, methods which employ relatively high levels of radiation which cause tissue damage generally are not preferred.

Autofluorescence has been used in attempts to detect cancerous tissue. Particularly, fluorescence occurs when certain substances called fluorophores emit light of a longer wavelength after being excited by light of another, shorter wavelength. The fluorescence which occurs in human and animal tissues is commonly referred to as autofluorescence because the fluorescence results from fluorophores occurring naturally in the tissues. The intensity of autofluorescence differs in normal and cancerous tissues, and autofluorescence can be used to detect cancerous tissue in different organs, including the colon, esophagus, breast, skin, and cervix.

In many medical and laboratory applications, the use of autofluorescence often is preferred for detecting cancerous tissue because autofluorescence avoids the introduction of exogenous fluorophores or any other exogenous agent. The use of exogenous agents increases costs and results in time delays due to lag in incorporating the exogenous agents into the examined tissue. Exogenous agents also introduce the risk of adverse reaction.

Known uses of autofluorescence are, however, limited to reliance on the non-specific autofluorescence emitted from extracellular components of whole tissue. Specifically, several extracellular components of whole tissue exhibit autofluorescence, including blood, blood vessels, collagen and elastin. These extracellular components may change in non-specific ways from normal to cancerous tissue. More specifically, known uses of autofluorescence to detect cancerous tissue cannot distinguish between cellular changes and non-specific extracellular changes from normal to cancerous tissue. Therefore, the application of the known uses of autofluorescence to detect cancer rely on non-specific autofluorescence and therefore cannot track cellular changes during the early stages of progression of cancer.

It would be desirable to provide apparatus and methods which facilitate the early detection of cancerous cells using autofluorescence. It also would be desirable to provide such autofluorescence apparatus and methods which exclude extracellular changes which are non-specific to cancer.

SUMMARY OF THE INVENTION

These and other objects may be attained by apparatus and methods for detecting the intensity of cellular autofluorescence which enable the early detection of cancerous cells and exclude extracellular changes which are non-specific to cancer. In one embodiment, the apparatus includes a light source for producing a beam of light to excite a tissue to emit cellular autofluorescence. The beam of light is first filtered through a narrow-band optical filter configured to pass light at a wavelength of about 280–300 nm, which is optimal for producing cellular autofluorescence. The beam of light is then transmitted to the tissue via a two-way fiber optic bundle having a sampling end positioned at or near the tissue being examined. A lens-system is positioned between the sampling end of the two-way fiber optic bundle and the tissue, and the lens system is configured to collect a light sample from the tissue. The light sample is transmitted back through the two-way fiber optic bundle and passes through a narrow-band optical filter configured to pass light at wavelengths of 320–340 nm. A photodetector positioned at the output end of the two-way fiber optic bundle measures the intensity of cellular autofluorescence emitted from the tissue.

In another aspect the present invention relates to a method for detecting pre-cancerous and cancerous cells in a tissue and in one embodiment, the method includes the steps of exciting the tissue with a beam of light delivered through a two-way fiber optic bundle, and measuring the intensity of cellular autofluorescence emitted from the tissue. The two-way fiber optic bundle may be inserted through the biopsy channel of an endoscope or through a needle inserted into the tissue. The light beam has a wavelength of about 280–300 nm, and the light sample is transmitted back through the two-way fiber optic bundle and through a narrow-band optical filter configured to pass light at wavelengths of 320–340 nm.

Measuring the intensity of the light sample at an emission wavelength of about 330 nm enables detection of pre-cancerous and cancerous cells. Specifically, the intensity of the light sample at 330 nm increases systematically with the progression of cancer from normal to cancerous tissue. In addition, at the wavelengths identified above, extracellular changes which are non-specific to cancer are excluded and therefore, only the cellular changes are detected. It is believed that the cell specific fluorescence originates from membranous structures in cells containing the amino acid Tryptophan.

DETAILED DESCRIPTION

The present invention is directed to apparatus and methods for detecting cancer in vitro and in vivo using cellular autofluorescence. Although specific embodiments of the apparatus and methods are described below, many variations and alternatives are possible. Also, the term tissue as used herein refers to both in vitro and in vivo tissues. In addition, the term tissue as used herein refers to tissue, organs (in vivo or in live animals or humans), as well as samples of cells, such as in cytology (examination of a film of cells on a glass slide). Further, the cancer detection apparatus and methods can be used in connection with the detection of early cancer, or pre-cancer, or dysplasia.

Figure 1:
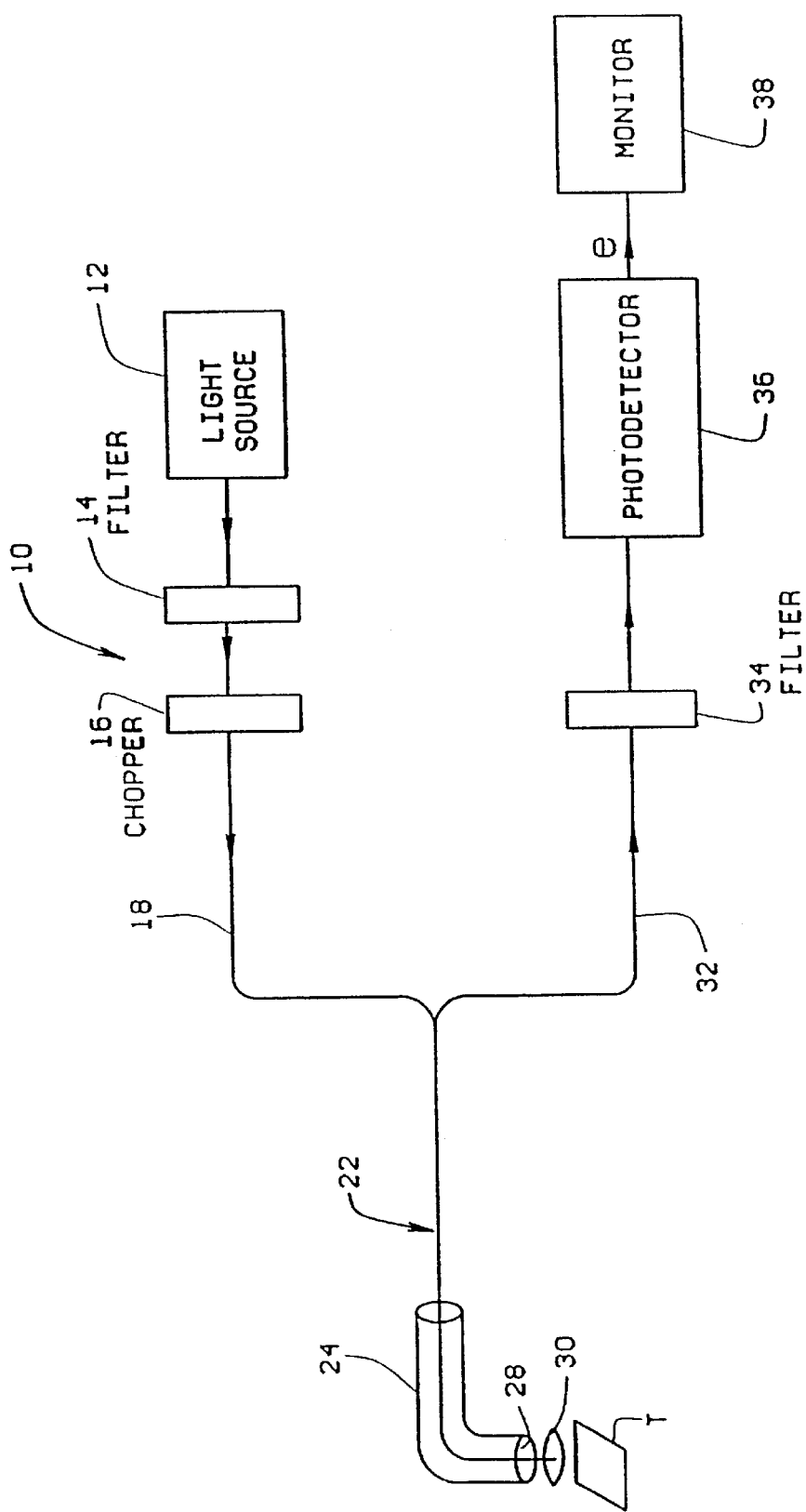
FIG. 1 is a schematic illustration of an apparatus for detection of cancer using cellular autofluorescence in accordance with one embodiment of the present invention.

Referring specifically to the drawings, FIG. 1 is a schematic view of an apparatus 10 for detecting cancer in vitro or in vivo using cellular autofluorescence. Apparatus 10 includes a light source 12, such as a Xenon arc lamp or a laser, powered by a conventional power source. A first optical filter 14 with a narrow bandwidth of about 20 nm, configured to pass light at a wavelength in a range of about 280–300 nm, is positioned in the path of the light beam produced by light source 12. The light beam emerging from first optical filter 14 passes through an optical chopper 16 which removes wavelengths of any background light. The light beam then passes through a two-way fiber optic bundle 22, sometimes referred to herein as a probe, which is positioned to catch the light beam as it emerges from optical chopper 16. The two-way fiber optic bundle 22 has a sampling end 28, and comprises two groups of optic fibers. A first group of optic fibers 18 transmits light from source of white light 12 to a tissue T. A second group of optic fibers 32 transmits a light sample back from tissue T for analysis.

The two optical fiber groups of two-way fiber optic probe 22 are randomly intermeshed. Two-way fiber optic probe 22 is less than about 2.5 mm in diameter and is long enough to pass through the biopsy channel of an endoscope, e.g., about 1–2 m in length. Specifically, probe 22 is configured to pass through the biopsy channel of a conventional endoscope 24, such as the endoscopes commonly used to examine the gastrointestinal tract or the lungs. In an alternate embodiment, two-way fiber optic bundle 22 may be passed through a needle or trocar to obtain measurements of cellular autofluorescence intensity from solid masses or organs such as breast, liver or pancreas.

A lens system 30 is positioned between sampling end 28 of two-way fiber optic bundle 22 and tissue T. Lens system 30 is provided to avoid direct contact between the tissue and probe 22. Light emerging from tissue T, including emissions of cellular autofluorescence and reflected and scattered light, is collected by lens system 30 to form a light sample.

The light sample is directed to sampling end 28 of two-way fiber optic bundle 22. The light sample is then transmitted back through two-way fiber optic bundle 22, along second group of optic fibers 32, from sampling end 28 to a second optical filter 34. Second optical filter 34 has a narrow bandwidth of about 20 nm, configured to pass light at a wavelength of about 320–340 nm, and is positioned in the path of the light sample transmitted back from tissue T. A photodetector 36 is positioned to collect the light sample as it emerges from second optical filter 34. Photodetector 36 is configured to measure the intensity of the light sample across wavelengths varying from about 320 nm to about 340 nm.

Photodetector 36 generates an electrical output signal e whose magnitude is proportional to the intensity of the light sample at a wavelength of about 330 nm. Electrical output signal e is amplified and displayed on a monitor 38 as a wave form or meter response. The intensity of cellular autofluorescence in tissue T may thus be noted and compared to the intensity of cellular autofluorescence at about 330 nm in a tissue whose condition is known, such as a cancerous, pre-cancerous or normal tissue. The presence of cancerous cells is indicated by an increase, relative to normal tissue, in intensity of cellular autofluorescence at an emission wavelength of about 330 nm. A ratio of the intensity of cellular autofluorescence in the tissue $F_t$ to the intensity of cellular autofluorescence in a known normal sample $F_n$ may be constructed. The greater the value of $F_t/F_n$, the more severe the degree of cancer or malignancy.

Figure 2:
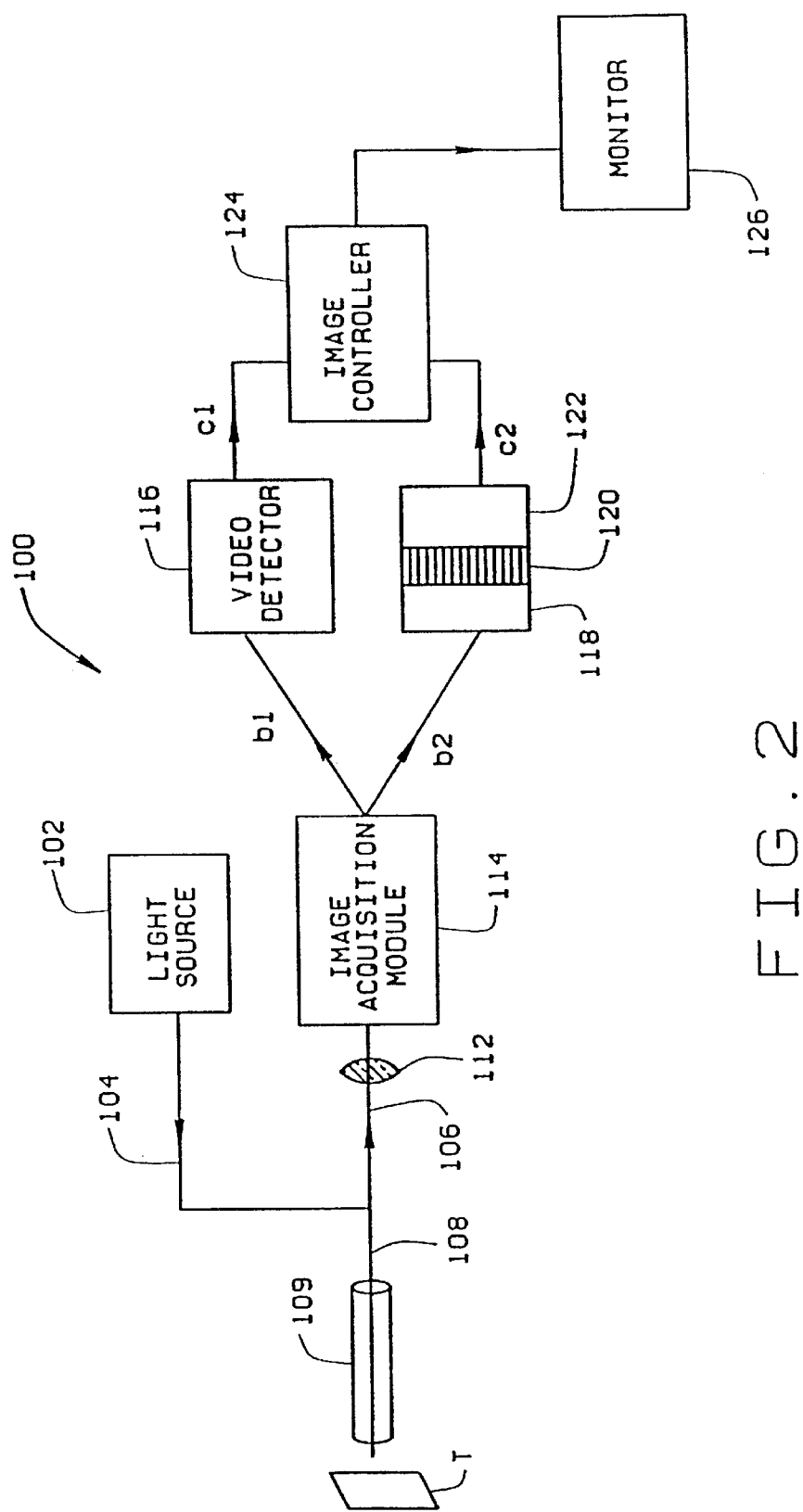
FIG. 2 is a schematic illustration of an apparatus for detection of cancer using cellular autofluorescence in accordance with another embodiment of the present invention.

FIG. 2 is a schematic view of an apparatus 100 for real time detection of cancer in vitro or in vivo using cellular autofluorescence and video imaging technology. Apparatus 100 includes a source of white light 102, such as a Xenon arc lamp or a laser, is powered by a conventional power source and produces a beam of light. The light beam then passes through a first group of optic fibers 104 of a two-way fiber optic bundle 108 which is positioned to catch the light beam as it emerges from white light source 102. The first group of optic fibers 104 transmits the light beam to a tissue T. Two-way optic fiber bundle 108 passes through a conventional endoscope 109. In alternate embodiments, the two-way fiber optic bundle may pass through a large-bore needle or trocar. A lens system 110 is part of the endoscope 109 and interposed between tissue T and two-way fiber optic bundle 108. It is positioned to catch reflected and scattered light from tissue T, as well as emissions of cellular autofluorescence, to form a light sample from tissue T. A second group of optic fibers 106 in two-way fiber optic bundle 108 transmits the light sample back from tissue T.

The light sample transmitted along second group of optic fibers 106 of two-way fiber optic bundle 108 is directed into an image acquisition module 114 by a lens 112. Image acquisition module 114 uses a standard optical device such as a prism or dichromatic mirror to split the light sample into two beams of light $b_1$ and $b_2$, each comprising identical wavelengths. Light beam b1 is transmitted to a conventional video detector 116 which produces a video signal c1 representative of the standard visual image obtained from tissue T with endoscope 109 and lens system 110. Light beam b2 is transmitted to an optical filter 118 with a bandwidth of about 20 nm at about 330 nm. Light beam b2 then impinges on an image intensifier 120, and then a charge-coupled device or CCD 122 which produces a second video signal c2. Video signal c2 is representative of the intensity of cellular autofluorescence emitted from tissue T. Video signal c2 is color-coded according to the intensity of cellular autofluorescence to visually represent different stages of malignancy of the lesian. Video signals c1 and c2 are then directed via conventional cable means to a computerized image controller 124 which combines the two video signals c1 and c2 into a single signal which represents the superimposition of the image represented by c2 onto the image represented by c1. The combined signal is then directed to a standard color video monitor 126 for display of the combined images.

Figure 3:
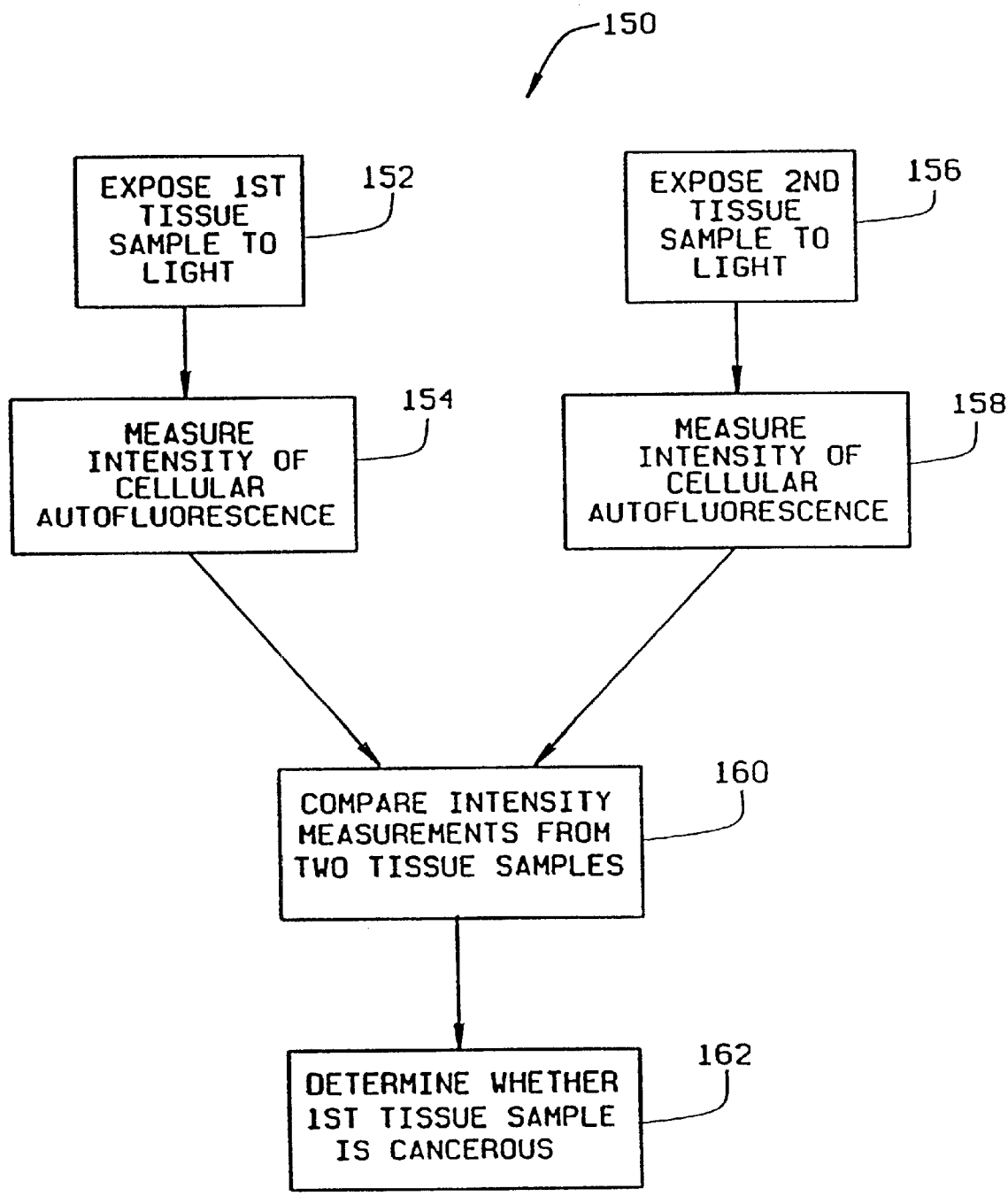
FIG. 3 is a flow chart illustrating a method for detection of cancer using cellular autofluorescence in accordance with an embodiment of the present invention.

FIG. 3 is a flow chart illustrating a method 150 for utilizing autofluorescence to detect pre-cancer, early cancer, cancer, and dysplasia. Method 150 includes exposing a first tissue to a light beam 152 which excites the tissue and results in an emission of cellular autofluorescence at a wavelength of about 330 nm. In this embodiment, the first tissue is being examined for the detection of cancer. After exposure of the tissue to the beam of light, the intensity of cellular autofluorescence emitted from the tissue is measured, at a wavelength of about 330 nm, using a standard photodetector 154.

In parallel, or in series, with steps 152 and 154, a second tissue whose condition is known as normal, pre-cancerous, or cancerous also is examined. Particularly, the second tissue is exposed to a light beam 156 which excites the tissue and results in an emission of cellular autofluorescence at a wavelength of about 330 nm. After exposure of the tissue to the beam of light, the intensity of cellular autofluorescence emitted from the tissue is measured, at a wavelength of about 330 nm, using a standard photodetector 158.

The intensity measurements from the first and second tissues are then compared 160. The intensity measurements obtained from the second tissue, which is of known condition, serves as a standard. Using the results of the comparison, the condition of the first tissue can be determined 162.

Method 150 may be practiced in vivo using a two-way fiber optic bundle passed through the biopsy channel of a conventional endoscope, as described above in connection with FIGS. 1 and 2. Alternatively, the first and second tissues may be collected tissue samples and method 150 may be practiced in a laboratory. In addition, method 150 could be practiced in connection with the use of a charge-coupled device and video imaging equipment. With such devices and equipment, and at steps 154 and 158, the intensity of the autofluorescence could be visually represented in a real time video image. Real time video scanning of cellular autofluorescence would allow large areas of tissue to be scanned both in vitro and in vivo.

Figure 4:
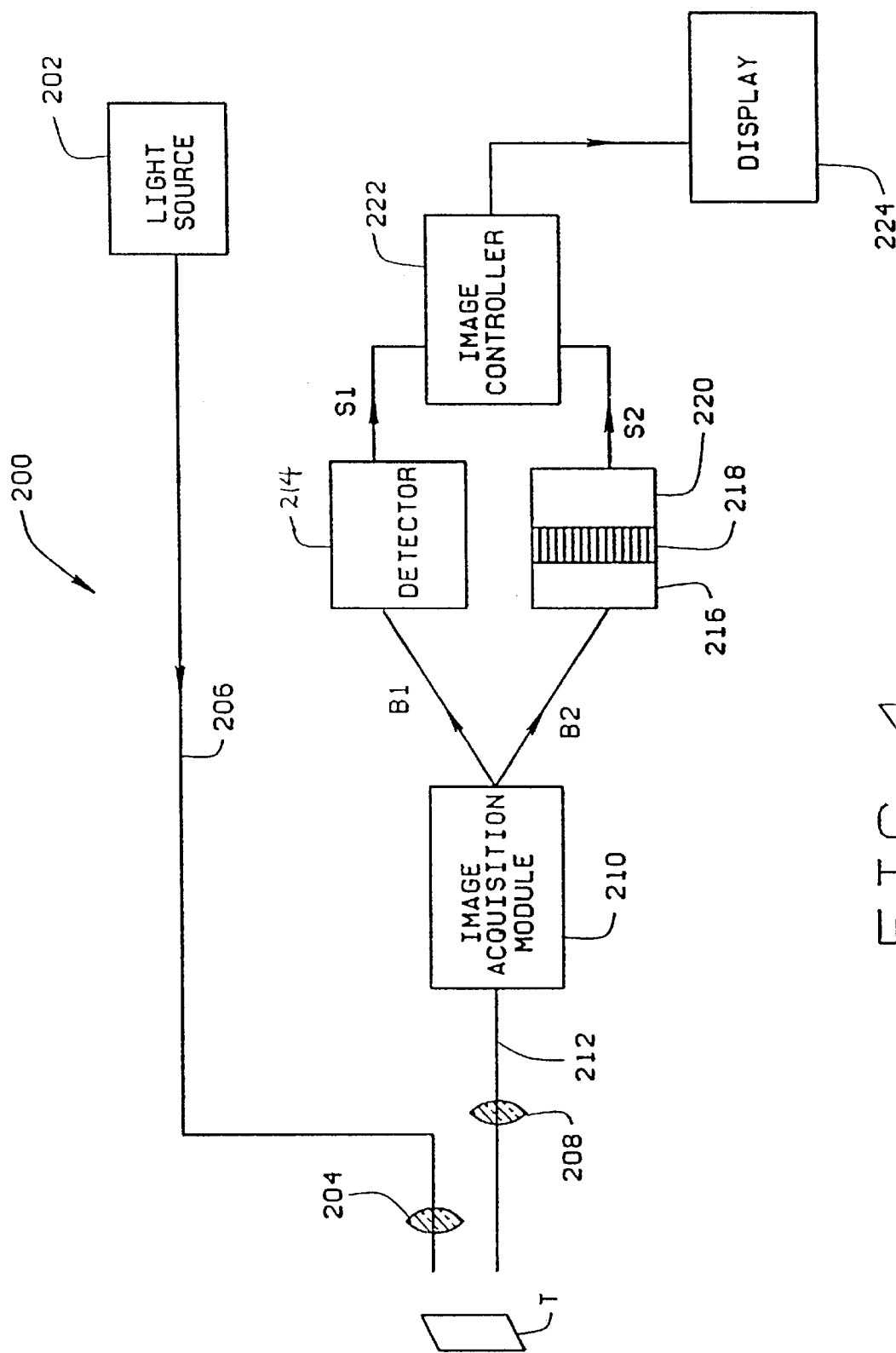
FIG. 4 is a schematic illustration of an apparatus for detection of cancer using cellular autofluorescence in accordance with yet another embodiment of the present invention.

FIG. 4 is a schematic illustration of an apparatus 200 for detection of cancer using cellular autofluorescence in accordance with yet another embodiment of the present invention. Apparatus 200 includes a light source 202 which may be a component of a conventional endoscopic illumination system. Light source may, for example, be a Xenon lamp or a source of laser energy. Source 202 is coupled to a lens system 204 by a optical fiber bundle 206. Lens system 204 is focused on a tissue T, such as a tissue, a tissue sample, an organ, or cells. A lens system 208 is positioned to collect light from tissue T, and lens system 208 is coupled to an image acquisition module 210 by an optical fiber bundle 212. At image module 210, the light received from bundle 212 is split using a splitter such as a dichromatic mirror or a prism to produce two identical beams B1 and B2.

Light beam B1 is transmitted to a conventional video detector 214 which produces a video signal S1 representative of the standard visual image obtained from tissue T. Light beam B2 is transmitted to an optical filter 216 with a band width of about 20 nm which allows wavelengths of about 290 nm (e.g., a range of about 280 nm to 300 nm) to pass through. Light beam B2 then impinges on an image intensifier 218, and then a charge-coupled device or CCD 220 which produces a second video signal S2. Video signal S2 is representative of the intensity of cellular autofluorescence emitted from tissue T.

Signals S1 and S2 are supplied to a computerized image controller 222 coupled to a display 224. The autofluorescence image from signal S2 could be color coded (i.e., different colors represent different grades of fluorescence intensities, and hence stages of malignancy) and superimposed on the standard endoscopic image from signal S1. The intensity of cellular fluorescence would be stronger in malignant tissues than in normal tissue of the same organ, for example. The intensity of malignant areas also would be greater than that in dysplastic areas, which should be stronger than that in normal areas. If a laser source is used as light source 202, a gating mechanism could be utilized to rapidly and alternately illuminate the sample with white light (for routine video endoscopy) and the laser (for fluorescence imaging).

Using the above described methods and apparatus, fluorescence images can be obtained during endoscopy, from gastrointestinal organs, lungs, bladder, ureters, cervix, skin and bile ducts, and pancreatic ducts. Narrow caliber endoscopes can be passed through the biopsy channels of larger endoscopes to obtain cellular fluorescence imaging from organs such as ureters, bile and pancreatic ducts, or may be passed through a large bore needle or trocar to examine solid organs such as the liver, pancreas, breast, prostrate, or other masses.

Measuring the intensity of the light sample at an emission wavelength of about 330 nm enables detection of pre-cancerous and cancerous cells. Specifically, the intensity of the light sample at 330 nm increases systematically with the progression of cancer from normal to cancerous tissue. In addition, at the wavelengths identified above, extracellular changes which are non-specific to cancer are excluded and therefore, only the cellular changes are detected. It is believed that the cell specific fluorescence originates from membranous structures in cells containing the amino acid Tryptophan.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A method of detecting cells which are cancerous, pre-cancerous or dysplastic, the method comprising exposing cells suspected of being cancerous, pre-cancerous or dysplastic to one ultraviolet light beam limited to wavelengths of about 280–300 nm, measuring one intensity of autofluorescence emission from the cells wherein said measuring one intensity of autofluorescence emission includes measuring autofluorescence emission at a wavelength in the range of about 320–340 nm and determining whether the cells are cancerous, pre-cancerous or dysplastic, wherein said determining consists of concluding that the cells are cancerous, pre-cancerous or dysplastic if said one intensity of autofluorescence emission is greater than that of cells which are not cancerous, pre-cancerous, or dysplastic.

2. The method of claim 1 wherein the measuring of autofluorescence emission measures cell specific fluorescence and excludes extracellular fluorescence.

3. The method of claim 2 wherein the measuring of autofluorescence emission measures cell specific fluorescence originating from tryptophan.

4. The method of claim 1 wherein said measuring one intensity of autofluorescelnce emission consists of measuring autofluorescence emission intensity at a wavelength of about 330 nm.

5. The method of claim 1 wherein the determining comprises determining ratio of intensity of cellular autofluorescence to intensity of autofluorescence in cells which are not cancerous, pre-cancerous or dysplastic.

6. The method of claim 5 further comprising assessing severity of cancer progression wherein a greater ratio indicates more severity in degree of cancer, pre-cancer or displasia.

7. The method of claim 1 wherein the cells are in vivo.

8. The method of claim 7 wherein exposing the cells to ultraviolet light comprises exposing the cells to a beam of ultraviolet light delivered through a two-way fiber optic bundle in an endoscope or in a needle.

9. The method of claim 1 wherein the cells are in vitro.

10. The method of claim 1 which detects cancerous cells.

11. The method of claim 1 which detects pre-cancerous cells.

12. The method of claim 1 which detects dysplastic cells.

13. The method of claim 1 wherein the cells which are not cancerous, pre-cancerous, or dysplastic are from the same organ type as the cells suspected which are suspected of being cancerous, pre-cancerous or dysplastic.

14. The method of claim 13 wherein the cells are from a gastrointestinal organ, lung, bladder, ureter, cervix, skin, bile duct or pancreatic duct.

* * * * *